United States Patent [19]

Chen et al.

[11] Patent Number: 5,188,715
[45] Date of Patent: Feb. 23, 1993

[54] CONDENSATE CORROSION SENSOR

[75] Inventors: Tzu-Yu Chen; Martin R. Godfrey, both of Naperville, Ill.

[73] Assignee: Nalco Chemical Company, Naperville, Ill.

[21] Appl. No.: 760,546

[22] Filed: Sep. 16, 1991

[51] Int. Cl.⁵ .................................... G01N 27/417
[52] U.S. Cl. ............................ 204/153.11; 204/404
[58] Field of Search ......................... 204/153.11, 404

[56] References Cited

U.S. PATENT DOCUMENTS

4,840,719 6/1989 Jasinski .............................. 204/404

Primary Examiner—Aaron Weisstuch
Attorney, Agent, or Firm—Kinzer, Plyer, Dorn, McEachran & Jambor

[57] ABSTRACT

An apparatus and method for measuring metal corrosion rate in solutions, including solutions having low ionic strength. Three electrodes including a counter-electrode, a reference electrode, and a working metal electrode are dispossed in close proximity to each other and an ion conducting, but electrically insulating, material is provided between at least the reference and working metal electrodes. The ion conducting material provides a pathway for ions to travel between the electrodes other than through the solution without also creating a short circuit between the electrodes.

11 Claims, 2 Drawing Sheets

CONDENSATE CORROSION SENSOR

BACKGROUND OF THE INVENTION

1. Field of the Invention

This invention relates generally to the measurement of corrosion rates and more particularly, the invention relates to an improved corrosion probe and method for rapidly measuring corrosion rates of metals in a corrosive or noncorrosive liquid environment where the measurements are made on-line.

2. Description of the Prior Art

Corrosion of condensate systems in boilers can cause costly component failures. Several presently used conventional condensate corrosion monitoring techniques utilize indirect methods of measurement of various processes which are indicative of the corrosivity of the environment being measured. These methods include measurements of conductivity, pH, iron or copper concentration and dissolved oxygen concentration. Because they measure indications of corrosivity only indirectly, none of these methods can provide information which may be necessary to the condensate system operator, such as the instantaneous corrosion rate.

Direct measurement of corrosion rate in a corrosive liquid environment is also an established procedure and can be performed on-line by inserting a probe into a moving or stationary liquid. One example of such a probe and method of measurement is described in U.S. Pat. No. 4,840,719, describing a process for measuring the corrosion rates of metals in a corrosive liquid environment by essentially inserting a probe into a corrosive liquid and electrically attaching the probe to a potentiostat. The measurement in a corrosive liquid, of high ionic strength, is facilitated by the rapid movement of the ions in the liquid between different electrodes in the probe.

A problem develops, however, when the corrosion rate of metals in a low ionic strength medium, such as distilled water, is being measured. Because there is a low concentration of ions in the liquid, charge cannot flow easily between the electrodes of the probe, thus rendering the measurement of the corrosion rate of the metals in contact with the liquid much more difficult and not possible within certain ranges.

For example, presently being sold in the United States is a prior art device for measuring corrosion rate of metals in liquid environments of strong or moderate ionic strength. This device includes probes and instruments which provide a direct measure of corrosion rate of metals in electrolytes by the technique of linear polarization resistance. The device interacts with the electrochemical corrosion mechanism in order to determine the rate at which metal ions are dissolving into solution. The passage of metal ions into solution is what causes corrosion of the metals.

The prior art device applies a small potential between metal electrodes and measures current flowing between the electrodes. The current depends on both the rate of the corrosion reaction and the resistance of the medium. Without a certain amount of ionic strength providing for conductivity in the medium, the instruments of the prior art devices cannot operate. Sale of the prior art devices, in fact, is often accompanied by sales literature which includes a graph indicating a nonoperative region of the device where the ionic conductivity of the medium is low, such as for rain water or distilled water or even boiler condensate water, as the medium in which corrosion is measured.

The need and desirability is recognized of a corrosion measuring instrument that is not limited by the lack of conductivity of the medium in which the measurements are being made.

SUMMARY OF THE INVENTION

Accordingly, it is one object of the present invention to provide a corrosion measurement device which is capable of measuring corrosion as well in a relatively nonconducting medium, such as distilled water, as in media of high ionic strength, such as sea water.

It is another object of the present invention to provide a portable, on-line corrosion measurement device which is easy to monitor and which can continuously take readings in all liquid environments, whether they contain ions or not.

In accordance with these and other objects, features and advantages, there is disclosed an apparatus for measuring metal corrosion rate in a solution comprising a counter electrode for providing current, a reference electrode to sense the potential of a working electrode, a working metal electrode being of the material of which corrosion is being determined, and an ionic conducting membrane disposed between at least the reference and working metal electrodes for providing a pathway for potential measurement between the working and reference electrodes.

Also disclosed is a method of measuring metal corrosion rate in a solution comprising, providing a probe, including a counter electrode, a reference electrode and a working metal electrode in close proximity to each other and electrically insulated one from another, disposing an electrically insulating ion conducting membrane between at least the reference electrode and the working metal electrode, contacting the probe to the test solution, measuring the current between the counter and working metal electrodes while varying the potential of the working electrode, utilizing the current and potential data to calculate the polarization resistance of the working metal electrode and calculating the corrosion rate from the value of the polarization resistance.

DETAILED DESCRIPTION OF THE INVENTION

Figures 1, 2, 4:
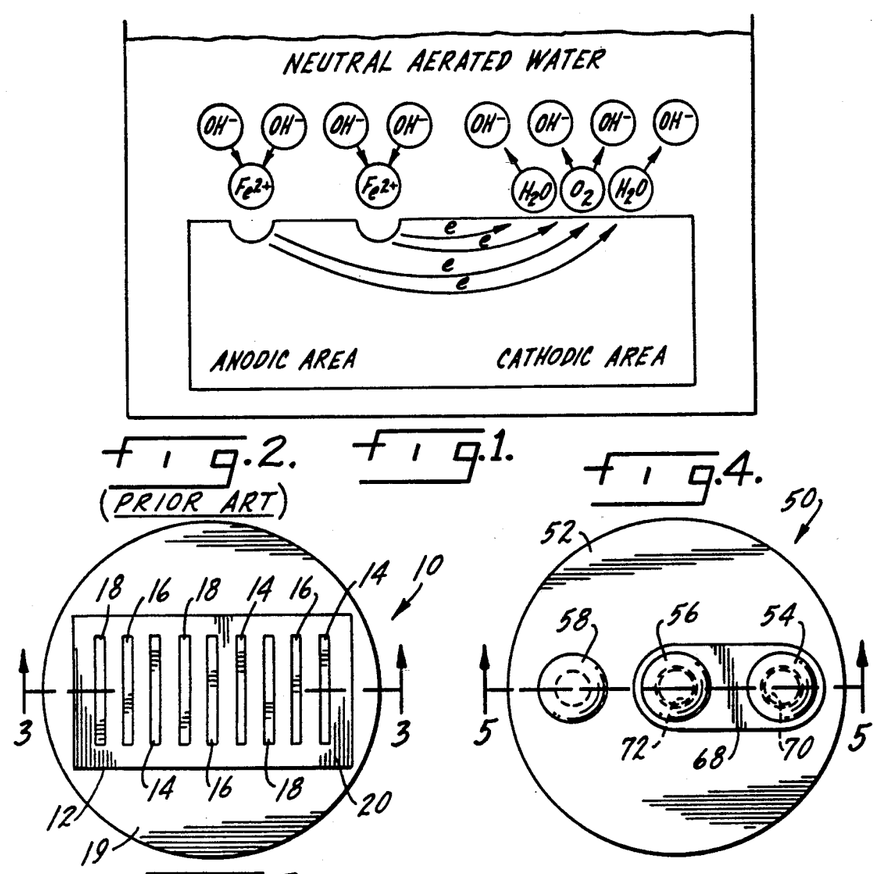
FIG. 1 is a schematic diagram of a typical corrosion mechanism of a metal in a liquid.
FIG. 2 is a top view of a previously used device known to have been used for direct measurement of the polarization resistance of a metal in crude oil.
FIG. 4 is a top view of the corrosion measurement device according to the present invention.

Virtually all corrosion processes, and especially those in a liquid medium, are electrochemical in nature. These require the presence of an anode, a cathode, an electrolyte and a circuit to connect the anode and cathode. FIG. 1 shows a schematic diagram of a simple reaction of iron in neutral aerated water. The example of this reaction essentially proceeds according to chemical equation (1).

$$2Fe + 2H_2O + O_2 \rightarrow 2Fe^{++} + 4OH^- \rightarrow 2Fe(OH)_2 \quad (1)$$

The corrosion reaction of Equation (1) comprises two complimentary and necessary reactions, namely the anodic reaction and the cathodic reaction. Equation 1 can be divided into the following reactions:

$$2Fe \longrightarrow 2Fe^{++} + 4e^- \quad (2)$$
anodic reaction (oxidation)

$$2H_2O + O_2 + 4e^- \longrightarrow 4OH^- \quad (3)$$
cathodic reaction (reduction)

$$2Fe^{++} + 4OH^- \longrightarrow 2Fe(OH)_2 \quad (4)$$
subsequent reaction in the water medium At the anode, the metal, in this case iron, "corrodes" to form metal ions which dissolve into solution, subsequently reacting with hydroxyl ions (OH$^-$) in solution to form ferrous and/or ferric hydroxide. The reaction releases electrons which are conducted through the metal to the cathode. At the cathode area, various reactions may occur to consume the electrons. In this case, water (H$_2$O) and dissolved oxygen (O$_2$) react to produce hydroxyl ions (OH$^-$).

For the case of general corrosion, the surface of the metal comprises a large number of small anodes and cathodes forming local corrosion cells. These local cells result from small differences in the metal or process fluid. Differences in the metal can result from grain boundaries, welding, anomalies during manufacturing, etc. Differences in the process fluid, or electrolyte can result from differing concentrations of oxygen, differing temperatures or other localized differences. For general corrosion, these anodic and cathodic areas are continuously changing, which cause all areas of the surface to be corroded evenly. Extensive corrosion may result in the failure, sometimes catastrophic, of the metal component.

It has been recognized that corrosion and the rate of corrosion thus depends on the electrochemical mechanism and interrelationship between the metal and the corrosivity of the liquid. Measurement of the electrochemical properties which lead to the reaction provides a direct indication of the corrosivity and corrosion rate in the system.

The rate at which the metal ions dissolve into the water is the corrosion rate, and a measurement of the electrons passing between the anode and cathode areas of FIG. 1, known as the corrosion current density or $i_{corr}$, would provide a precise measurement of the corrosion rate. Thus, measurement of corrosion is a process which essentially requires monitoring of the electrochemical resistance at the metal-liquid interface. If $i_{corr}$ could be determined between each of the localized areas of the metal which form the anode and cathode between which the electrons pass, the precise mass of metal passing into solution could be calculated with a knowledge of the corrosion reaction. However, it is not possible to measure $i_{corr}$ directly in a single metal piece, since the anode and cathode areas are adjacent each other on the same piece of material, and the electron paths through the metal are diffused to the areas where one or another step in the reaction is occurring.

It has been determined that the resistance at the metal-liquid interface provides a direct indication of corrosion current density because this polarization resistance is inversely proportional to the rate of the corrosion reaction. Application of a small potential to a probe, which includes at least two electrodes made from the identical material as that under test, and measurement of the resulting current, provides an accurate measurement of the polarization resistance provided that the apparent resistance of the liquid is negligible.

The current between the electrodes is controlled by the same anodic and cathodic corrosion reactions that control the corrosion current. If the electrodes are corroding at a high rate with metal ions passing easily into solution, a small potential applied between the electrodes produces a high current or low polarization resistance. Conversely, if the electrodes are corroding at a low rate with the ions passing only slowly into solution, a small potential applied between the electrodes produces only a low current or high polarization resistance. Hence, by applying a small potential between the metal electrodes, a high current (low polarization resistance) corresponds to a high corrosion rate and low current (high polarization resistance) corresponds to low corrosion rate. As only small potentials are applied between the electrodes, the natural corrosion process which is occurring on the metal surface is not significantly disturbed.

A detailed electrochemical analysis of these types of reactions was performed by M. Stern and A. L. Geary who demonstrated, in the *Journal of the Electrochemical Society*, Vol. 4, p. 56, (1957), that the corrosion current density, $i_{corr}$ for small applied potentials followed values according to Equation (5).

$$i_{corr} = \frac{1}{2.303} \frac{B_a B_c}{B_a + B_c} \frac{1}{R_p A} \quad (5)$$

where $i_{corr}$ is the corrosion rate in terms of current density, $B_a$ and $B_c$ are the anodic and cathodic Tafel slopes, respectively, $R_p$ is the polarization resistance, and A is the electrode area.

The electrode area (A) is easily measured for well defined geometries. The Tafel slopes ($B_a$, $B_c$) can be determined by a well-known extrapolation process. Thus is can be seen that the polarization resistance ($R_p$) can be used as a direct measure of the corrosion rate since it is inversely proportional to the corrosion current density ($i_{corr}$)

Techniques exist for utilizing the Stern-Geary equation to determine corrosion rate of a metal by application of electrochemical methods. One such is the linear polarization technique. Sensors utilizing this technique are known as electrochemical polarization resistance probes.

In a typically performed linear polarization experiment, a ±10 mV voltage signal is applied across the corroding interface to measure the total resistance of the system, $R_2 + R_p$. Here $R_s$ is the solution resistance representing 25 the resistance of the test environment itself; and $R_p$ is the polarization resistance, as in the above equation (5).

A major disadvantage of this type of sensor is that it cannot be used in low conductivity media, including condensate water. Attempting to measure corrosion rate with such a sensor will significantly underestimate the actual corrosion rate. The error arises from the high solution resistance of environments that contain inadequate ionic electrolyte to conduct the current in the linear polarization measurement. Such environments include at least rain water, boiler condensate water, lubricating oil, crude oil and other organic solvents.

The solution resistance $R_s$ will appear in any measurement of total resistance of the probe electrodes. Use of the linear polarization technique with high conductivity media is possible because the solution resistance $R_s$ is at most a small portion of the total resistance. This fact permits the approximation of Equation (6):

$$R_s + R_p \approx R_p \qquad (6)$$

i e., that the total resistance is approximately equal to the polarization resistance. This approximation thus allows for use of the Stern-Geary equation (5) with accurate results for high conductivity media, such as salt water having high ionic strength. As the conductivity of the medium being tested decreases, however, the approximation is less valid and the results become less accurate. This results because the readings of polarization resistance, are increasingly skewed by the increasing value measured which is attributable to solution resistance. Thus the corrosion rate is underestimated, and in certain cases, to a greater degree, because of faulty interpretation of resistance readings.

One prior art device, discussed above, takes the solution resistance into account and provides a conductivity correction factor. Even with such a correction, however, resistance cannot be accurately measured for metals in a liquid in which the conductivity is lower than in good quality drinking water. Accordingly, measurement of resistance for condensate water becomes doubtful and the readings of prior art devices become essentially meaningless. These devices are thus inoperable in the lower conductivity ranges.

The invention herein consists of a device which is able to measure polarization resistance ($R_p$) while simultaneously reducing the magnitude of the measured solution resistance which derives from the test media or solution. The invention recognizes that the problem of accurate resistance measurement in a test solution having low conductivity derives from the unavailability of a mechanism or means for the continuous migration of ions between the working electrode and the reference or counter electrodes of the probe. The invention thus provides for just such a mechanism, eliminating the measurement of the solution resistance $R_s$, and providing a much more accurate measurement of the polarization resistance $R_p$. This in turn more accurately measures the corrosion current density ($i_{corr}$) and provides a more precise and accurate reading of the corrosion rate.

Figure 3:
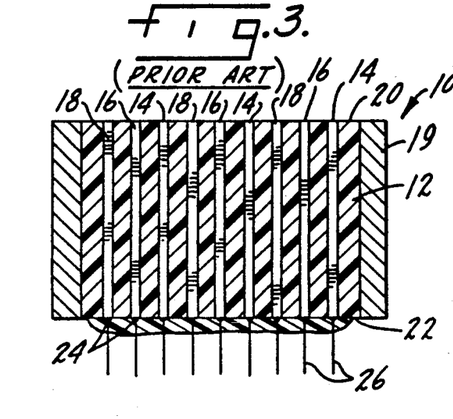
FIG. 3 is a cross-sectional view of the device illustrated in FIG. 2 taken approximately along the line III—III.

Referring now to FIGS. 2 and 3, a probe 10, according to the prior art disclosed in U.S. Pat. No. 4,840,719, is shown. FIGS. 2 and 3 illustrate a top view and a cross-sectional view, respectively, of the prior art device described in U.S. Pat. No. 4,840,719.

The conventional probe 10 shown in FIGS. 2 and 3 comprises a phenolic mount 12 molded from an appropriate nonconductive phenolic resin, such as a phenolic red bakelite compound which is commercially available from Leco Corporation in St. Joseph, Missouri. The mount 12 is molded around a series of electrodes grouped in sets, each set containing three electrodes, the working electrode 14, the reference electrode 16 and the counter electrode 18. At least one of these electrodes, the working electrode 14, is made of the test metal for which the corrosion rate is being tested. For example, if the pipe (not shown) in which the test liquid is flowing through is carbon steel, then the working electrode 14 ideally must be made from the same composition carbon steel.

The electrodes are embedded in the mount 12, which itself is surrounded by a retaining material 19. The electrode ends, which are visible at the working surface 20 of the probe, are clear of the material forming the mount 12 so as to be able to contact the test liquid or medium.

The probe 10 is utilized by placing it through an opening in a pipe or container (not shown) so that the working surface 20 of the probe 10 is in contact with the liquid for which corrosion is being tested. The working surface 20 is bordered by retaining material 19 which acts as an insulator. On the electrical connection surface 22 of the mount 12, which is opposite the working surface 20, each of the electrodes 14, 16, 18 is connected by solder 24 or other means to lead wires 26, which in turn are connected to a voltage source, and sensing and analyzing equipment (none of which is shown).

The phenolic resin comprising the mount 12 is a dielectric material and therefore insulates the electrodes 14, 16 and 18 from each other. Nevertheless, the working surface 20 of the mount 12 is artificially made ionically conductive. The ionically conductive surface is obtained by the method disclosed in U.S. Pat. No. 4,840,719, which comprises introducing or embedding "artificial" charge carriers within the phenolic resin material of the working surface 20. One embodiment disclosed in U.S. Pat. No. 4,840,719 includes immersing surface 20 in a solution of potassium hydroxide (KOH) or a mixture of KOH and $H_2O_2$, until a surface film of the phenolic resin along surface 20 is impregnated with the ionically conductive material, e.g. $OH^-$. That film, when it is placed within a test liquid, provides a path or transmission mechanism for ions to flow between electrodes. Despite the conductivity of the film to ions, the film itself, like the remainder of the phenolic resin of mount 12, is not electrically conductive and thus will not create a short circuit between the electrodes when an electrical potential is applied across them.

It has been determined, however, that the device according to U.S. Pat. No. 4,840,719 is not capable of continued reliability for long periods of time. For example, continued immersion of the probe 10 in a pure water medium was found to result in a leaching of the $OH^-$ out of the film providing the ionically conductive surface 20. The continued leaching of the $OH^-$ leads to inconsistent results in measurements made in identical conditions and after a period the probe becomes inoperable.

Figure 5:
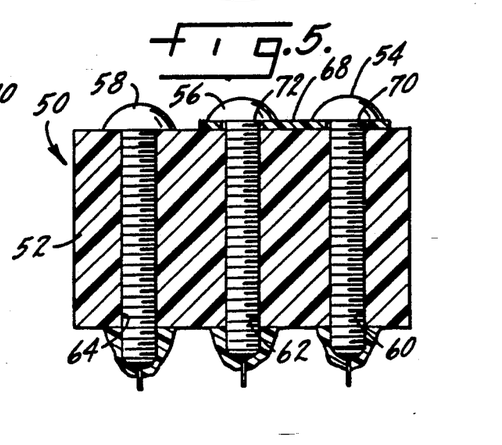
FIG. 5 is a cross-sectional view of the device illustrated in FIG. 4, the cross section being taken approximately along the line V—V.

Referring now to FIGS. 4 and 5, a probe 50 according to the invention is illustrated, with FIG. 5 being a cross section of the probe 50 shown in FIG. 4 as taken approximately along line V—V.

The inventive probe 50 shown in FIGS. 4 and 5 comprises a mount 52 comprising a dielectric, insulating material such as bakelite or Teflon, which surrounds a set of three electrodes, a working electrode 54, a reference electrode 56, and a counter electrode 58. The cross-sectional view of FIG. 5 more clearly shows the electrodes 54,56,58 as screws which are molded into the material comprising mount 52. Alternatively, the electrodes 54,56,58 may be screws which are screwed into threaded holes 60,62,64, respectively, disposed in the mount 52. The alternative arrangement may be necessary if corrosion testing is consecutively performed on pipes comprising different media. For example, if the electrodes 54,56,58 comprise carbon steel for measuring corrosion of a carbon steel pipe (not shown), and the testing system must then be moved to a copper pipe (not shown), the electrodes 54,56,58 may be unscrewed and replaced with electrodes comprising copper identical to the composition of the pipe in which corrosion testing is to be then performed.

When the probe 50 is placed into a test liquid in which the corrosion rate is to be measured, the probe is fit through a pipe and a working surface contacts the adjacent test liquid (not shown). Each of the electrodes 54,56,58 are in contact with the test liquid. The test liquid may have high ionic conductivity, as does sea water, in which case the liquid will be capable of passing ions between the electrodes 54,56,58.

As described above, a flow path for ions is necessary between at least the working electrode 54 and the reference electrode 56. In a preferred embodiment, an additional ion flow path between the working 54 and counter 58 electrodes is provided to reduce the resistance between these two electrodes and to avoid problems that may occur from the potentiostat used to measure the polarization resistance.

Such a flow path is provided in the invention by means of a distinct, separate washer 68 or other type of nonsoluble solid material, which acts as a salt bridge between at least the working and reference electrodes 54,56. Preferably, the form of the solid material comprises a flat washer 68 having at least two holes 70,72 spaced from each other so that the holes 70,72 overlie the holes 60,62 in the mount 52. The screws comprising electrodes 54,56 can then be inserted first through the holes 70,72 and then through holes 60,62, respectively.

The washer 68 comprises a distinctive material known as a perfluorinated ion exchange membrane which is manufactured by DuPont Company, Polymer Products Department, under the brand name NAFION. NAFION material may comprise compositions, for example:

or:

-continued

This material has the property of being able to pass through a positive ion, such as $Na^+$.

A major advantage in the use of a NAFION membrane is that the material is thermally stable and chemically inert. These properties arise from the use of perfluorinated monomers in the synthesis of the material. The ionic conductivity of NAFION is provided by perfluorinated polypropylene oxide side chains that are terminated with sulfonic ($SO_3H$) or carboxylic ($COOH$) acid groups. Other materials can be used in substitution of the NAFION as the washer 68 in the probe 50, as long as the material is a thermally stable, chemically relatively inert polymer or other solid electrolyte that has ionic conductivity at the test temperature.

Tests of a probe 50 utilizing the NAFION material washers 68 have provided favorable results. The NAFION material comprising the washer 68 utilized in these tests was of a type known as NAFION/$H^+$ that is available from DuPont and which has an ionic form utilizing $H^+$ ions. This material will be referred to herein as NAFION/$H^+$. Another type of NAFION material, NAFION/$Na^+$, has been found to work equally as well. It is believed that other alkali metals such as potassium (K), may be relied on as ionic charge carriers and possibly even iron (Fe) ions may be utilized for the purpose.

An alternative form of the NAFION material includes a $Na^+$ ionic form and is referred to as NAFION/$Na^+$. The inventors' tests have developed that both the NAFION/$H^+$ and NAFION/$Na^+$ forms, when utilized as a washer 68, produced more consistent results from the probe 50 than did a probe 10 which utilized an impregnated phenolic mount according to the prior art disclosure. Transition metal or alkali earth ions have been found to provide sensor performance that is substantially on a par with other sensors.

A feature of the invention provides for long term corrosion monitoring which includes the regeneration of the NAFION material washers 68 at predetermined time intervals. Regeneration may be necessary at these time intervals in order to maintain the desired ion conductivity in the washer 68 and is preferably accomplished by immersing the probe 50 into an appropriate $Na^+$ containing solution for a short period of time. Such a solution may comprise sodium borate, sodium perchlorate or sodium sulfate. Alternatively, the washer 68 itself may be replaced at periodic time intervals.

Figure 6:
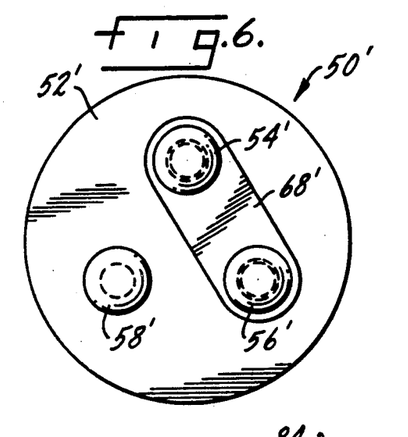
FIGS. 6, 7, and 8 are alternative embodiments of the device according to the present invention.
Figure 7:
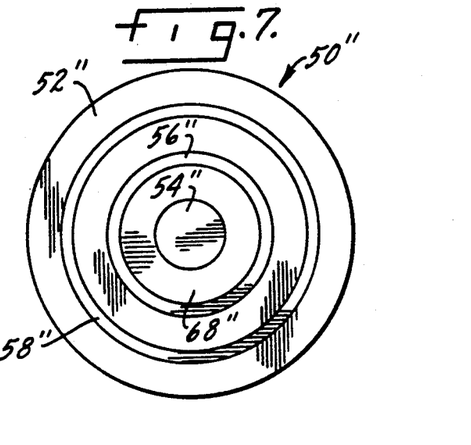

Referring now to FIGS. 6 and 7, there are illustrated two alternative embodiments of a probe similar to probe 50, having alternative configuration for the electrodes in the same plane. The electrode configuration is the important difference between the probes illustrated in FIGS. 6 and 7 and the probe 50 of FIG. 4. Appropriate structural differences may exist in the body of each of the probes of FIGS. 6 and 7 to take into account the alternative electrode configuration at the working surface, but all electrical connections and insulating characteristics remain essentially the same. Accordingly, similar elements in the probes shown in FIGS. 6 and 7 will be referenced with identical numerals, but the reference numerals of FIG. 6 are referenced with a prime and the reference numerals of FIG. 7 are referenced with a double prime.

Referring now to FIG. 6, there is illustrated an alternative configuration probe 50' comprising a working surface 52' on which are disposed three electrodes, a working electrode 54', a reference electrode 56' and a counter electrode 58'. It has been found that a close packed configuration of the electrodes also provides accurate readings of corrosion rate because of the minimization of the travel path which the ions must traverse. The NAFION material 68' between the working electrode 54' and the reference electrode 56' and provides an identical function to that provided by the NAFION material 68 of probe 50.

FIG. 7 illustrates another probe 50" having three electrodes in a concentric configuration. The probe 50" comprises a working surface 52" on which is disposed a working electrode 54" having a plug construction similar to that of working electrode 54, shown in FIG. 4. However, reference electrode 56" is a circular metal band within the plane of working surface 52" that surrounds working electrode 54" in a concentric relationship. The concentric relationship provides a symmetrical and more uniform path for ion travel between the electrodes, and tends to avoid some of the circuitous travel paths encountered by ions traveling between the extreme removed portions of electrodes 54,56. Counter electrode 58" has a similar concentric relationship, albeit with a greater diameter than that of electrode 56". An important consideration of the electrode construction, however, is the requirement that the area of the working electrode 54 must be known so as to permit proper measurement of the polarization resistance and the corrosion rate.

Another consideration entering into the construction of the probe 50" is fabrication of the NAFION material 68". The NAFION material 68" is of a unitary construction having a number of holes at the center and close to the perimeter for providing the connections to the leads (not shown) which are connected to the underside of the electrodes 54" and 56". Thus a majority of the underside of the reference electrode 56" is in contact with the NAFION material 68"', the ion flow path between working electrode 54" and reference electrode 56" is a direct path.

Another method of manufacture of the probe 50" is the chemical plating of the electrodes onto the surface of a NAFION material membrane. For example, one side of a sheet of NAFION is exposed to a solution containing a salt of the metal which is desired for corrosion testing. The other face of the NAFION sheet is exposed to a solution containing a strong reductant, such as hydrazine. The reductant diffuses through the NAFION sheet and reacts with the metal ions on the opposite side, thereby forming a metallic coating on the NAFION material surface. Leads, which may comprise platinum or other noble metal, can then be connected to these coatings to form the electrodes.

Figure 8:
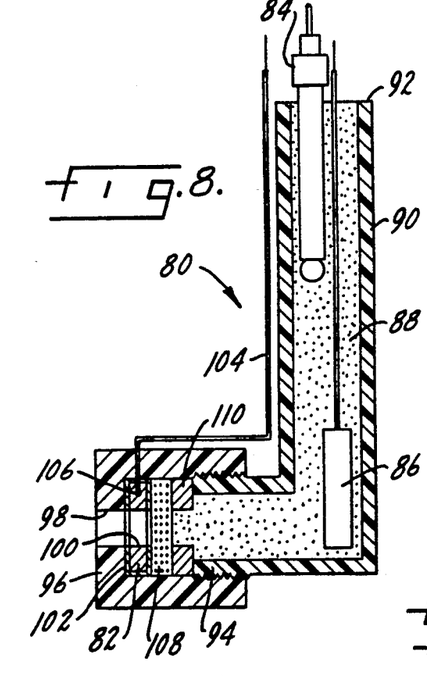

Another alternative is to provide a constant source of Na+ ions by a modification of the probe design. FIG. 8 illustrates an alternative embodiment of the inventive corrosion rate measurement sensor. A probe 80 comprises a working electrode 82 made from a steel washer, a conventional reference electrode 84, the details of which will be more fully described below, and a counter electrode 86. Each of the electrodes 82,84,86 perform identical functions as the electrodes in the probe 50, but as will be described, the probe 80 shown in FIG. 8 performs those functions in a different way than the probe 50.

Probe 80 includes a sensor compartment 88 which is enclosed by a NYLON or TEFLON tube 90, shown in cross section in FIG. 8. A stainless steel tube 90 is best utilized in high pressure, high temperature environments. One end of the tube 90, referenced here as the upper end 92, may be sealed or may be open to the atmosphere as shown. Upper end 92 may also be used for introduction of electrodes 84,86 into the sensor compartment 88.

A second end of the tube 90, referenced as the lower end 94, provides the direct contact of the probe 80 with the liquid test environment for which the corrosion rate is being measured. Lower end 94 of the tube 90 is enclosed by a cap member 96, which may also be made of a NYLON, TEFLON or stainless steel material. Cap member 96 is attached to lower end 94 by a threaded connection as shown, or by other appropriate means.

Cap member 96 includes a cap opening 98 which provides access to the lower end 94 and to the sensor compartment 88. The working electrode 82 is disposed immediately adjacent the cap opening 98. To maintain the area of working electrode 82 a known constant value, a simple, well-defined geometry is used for the portion of the electrode 82 which is available to the test liquid.

In the embodiment of FIG. 8, a steel washer is used and comprises electrode 82. After the galvanized zinc coating has been removed by a 10% HCl solution, the washer may be further polished to limit variation in surface area due to pits, scratches and other deformities. The peripheral surface 100 of the inside diameter of the washer provides the only direct contact of electrode 82 with the test liquid. The other three surfaces of electrode 82 are coated with a layer 102 of commercially available MICROSTOP paint, a dielectric material which insulates the noncontacting surfaces of the washer.

For even greater control of the electrode 82 surface area exposed to the test liquid, the inside diameter 100 of the washer may be polished, as with silicon carbide paper having up to 600 grit finishing. Polishing of inside surface 100 smoothes the surface of any remaining pits or protuberances, and provides an accurate indication of the electrode surface area which will contact the test liquid. A preferable value of the surface area available for exposure to the test liquid has been found to be approximately 0.11 $cm^2$ for a washer moving a thickness of 0.05 cm and an inside diameter of 0.7 cm.

Another feature of the invention apparent in FIG. 8 is that the inside diameter surface 100 of the washer electrode 82 is similar to inside diameter of the cap opening 98. Thus, the inside surface of cap 96 also surrounds two other surfaces of washer electrode 82 while keeping inside surface 100 free for direct exposure to the test liquid.

Electrode 82 also provides for an electrical connection to the monitoring and analysis equipment (not shown) by a shielded copper wire 104 which is soldered to the electrode 82 at a soldering point 106. Soldering of the wire 104 before application of the MICROSTOP paint coating 102 ensures that the electrical connection remains insulated from the environment.

Adjacent and abutting the other surface of washer electrode 82 is a NAFION "screen" 108 which encloses the compartment 88 by creating a plug for the cap opening 98 and the opening defined by the inside surface 100 of washer electrode 82. Compartment 88 is filled with a solution of sodium salt, such as $NaClO_4$, which ensures that the NAFION screen 108 is always saturated with $Na^+$ ions.

The electrical current created by the potential between working electrode 82 and the reference electrode 84 can pass through the NAFION screen 108 by means of the movement of the ionic species, such as $Na^+$ in the NAFION material and in the sensor compartment and $Fe^{++}$ near the NAFION material surface in the test water, and no supporting electrolyte is required. The starting NAFION screen then can be of the form NAFION/$H^+$, and will take on the $Na^+$ ions from the solution in the compartment 88. The NAFION screen 108 will screen out the negatively charged ions, such as $ClO_4-$, which may remain in solution in the sensor compartment. A TEFLON washer 110, having the same inside diameter as the steel washer electrode 82, can be utilized as a backing support for the NAFION screen 108.

An alternative probe, for use in a high pressure, high temperature environment, as discussed above, requires a stainless steel tube 90 and cap 96. With such a probe for use in a high pressure environment, a thick porous plug (not shown) may be used in place of the TEFLON washer 110 for added backing support to the NAFION screen 108. Such a porous plug may comprise any porous ceramic, for example zirconia, which can pass liquid and a salt solution through the pores, but may nevertheless remain solid enough to back up the NAFION screen without detracting from its ion transmitting characteristics.

The reference electrode 84 is an absolute voltage reference for the system, and provides a consistent reference point for measure of the exact voltage potential and indirectly, the polarization resistance at the interface of the test water and the working electrode 82. A well known reference cell, such as an Ag/AgCl cell can be utilized to provide an exact measure of the electrical potential, if more accurate results are desired.

The probe 80 is suitable and most effective in requirements of long term corrosion monitoring in pure water or other low conductivity media. The absolute measurements permitted by the reference cell comprising electrode 84 gives rise to the potential of the probe 80 to measure and monitor both the corrosion rate and the corrosion potential, either continuously or at discrete intervals, for extended periods of time. Other features of this embodiment will, of course, become evident to a person of ordinary skill in the art after grasping a complete appreciation of this invention.

Figure 9A:
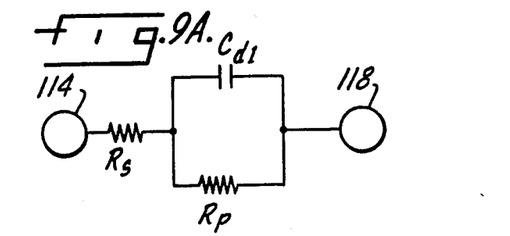
FIGS. 9A, 9B, 10A, and 10B are circuit diagrams which are schematically equivalent to the circuits formed by the various probes illustrated in FIGS. 2 and 4.

Referring now to FIGS. 9A, 9B, 10A and 10B, these figures show schematic circuit diagrams which may be considered the schematic equivalents of the probes 10, 50, 50' and 50" and the schematic circuit diagrams representative of the illustrated embodiments. FIG. 9A schematically illustrates the equivalent circuit of a prior art probe measuring resistance in a medium having low ionic conductivity, e.g. distilled water. The prior art device makes no provision for including a NAFION material membrane in combination with the electrodes. In the prior art device, $OH^-$ ions attached to the phenolic mount were found to leach out into the solution during distilled water tests. The schematic representation indicates the reference electrode as element 114, and the working electrode as element 118. The counter electrode is omitted from the circuit diagram of FIG. 9A. The leaching out of $OH^-$ ions from the phenolic mount of the prior art device tended to shift the equivalent schematic diagram representation of the prior art probe toward the one illustrated in FIG. 9A.

The schematic representation is provided to illustrate the manner in which the device is believed to operate. However, other interpretations and schematic representations may be more appropriate or better represent the observed phenomena. An example of another representative equivalent circuit may include a representation of the membrane capacitance for the NAFION material, as will be discussed below.

The diagram of FIG. 9A schematically illustrates the circuit formed between the electrodes, having elements defined by the test solution and by the electrode/solution interface. The electrical elements indicated each represent the following corresponding characteristics of the system formed by the probe and test solution:

$R_p$ = Polarization resistance.
$R_s$ = Solution resistance of electrolyte between the reference and working electrodes.
$C_{dl}$ = Double layer capacitance of liquid/metal interface.

A small potential, of approximately ±10 mV, is applied between the working and reference electrodes 114,118 at a very low potential scan rate, e.g. 0.1 mV/second, typically used with the linear polarization technique. At lower potential scan rate, the capacitor acts to emulate an open circuit condition and the current will flow through the resistive elements $R_s$ and $R_p$. From the measured current and the applied voltage, the total resistance $R_p + R_s$ may be determined by Ohm's law.

Figure 9B:
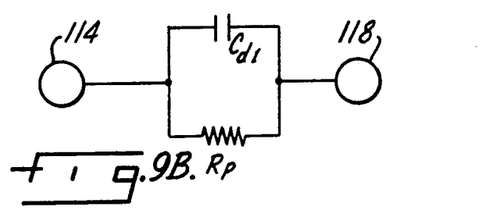

As has been described above, low solution resistance, or high ionic conductivity, represented as $R_s << R_p$, provides for the approximation wherein $R_s$ is ignored, and the measured resistance is considered to be the polarization resistance, $R_p$. An equivalent schematic circuit diagram, taking this approximation into account, is shown in FIG. 9B. From the polarization resistance $R_p$, the corrosion rate can be determined from an empirical determination of the appropriate constants.

However, when the solution resistance $R_s$ is high, i.e., ionic conductivity is low, the approximation cannot be made. In very low ion conductive media, such as distilled water, making such an approximation leads to a gross underestimation of the corrosion rates, and any resistance measurements obtained may be effectively disregarded. The equivalent circuit for the case of the solution resistance $R_s$ being much greater than the polarization resistance $R_p$ is represented by the schematic diagram of FIG. 9A where both $R_s$ and $R_p$ must be determined to obtain a reading of corrosion rate.

Figure 10A:
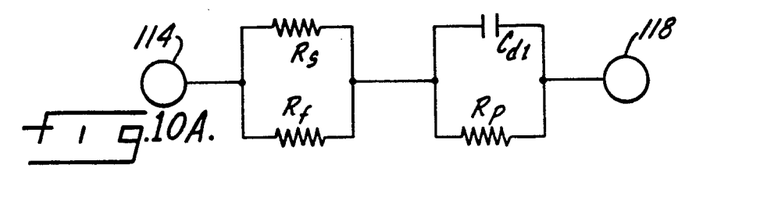

Introduction of a NAFION "salt bridge" membrane, such as NAFION washer 68 in FIG. 4, furnishes a polymeric path for ionic conduction. By careful probe design construction, the effects of the solution resistance is minimized and more accurate readings of the polarization resistance is possible. FIG. 10A illustrates the equivalent circuit diagram of the inventive probe, such as that shown in FIGS. 4-7, where all the schematically represented electrical elements represent the identical elements as in FIG. 9A. $R_f$ represents membrane resistance of the NAFION material element.

As discussed above, other equivalent represented by schematic circuit diagrams are possible. For example, in the presence of the NAFION material membrane, another capacitor may be added in parallel with the membrane resistance $R_f$ to indicate membrane capacitance $C_f$.

Figure 10B:
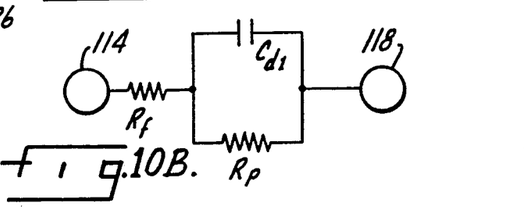

In most cases, the solution resistance $R_s$ is much greater than the membrane resistance $R_f$, i.e. ($R_s >> R_f$), and the diagram of FIG. 10A can be approximated to the diagram shown in FIG. 10B. This approximation is valid for the case of pure water or similar media, such as boiler condensate water. The approximation and schematic diagram of FIG. 10B essentially represents that the ionic flow path is through the NAFION material element 68, and essentially bypasses any ion flow through the test solution because of the much greater relative resistance of the solution. In the event that the value of the polarization resistance is very close to that of the NAFION membrane resistance, the resistance of the NAFION element 68 can be empirically determined and the value of the membrane resistance can be accounted for. Subtracting that value from the total resistance measured will provide a reading of polarization resistance $R_p$ and a simple calculation will furnish the polarization resistance $R_p$ and consequently the corrosion rate.

For cases in which $R_s$ is much less than $R_f$, e.g. solutions of high ionic strength, the probe according to the present invention is still operational. For such a case, the equivalent circuit illustrated in FIG. 10A can be even further simplified, since $R_s << R_f$. The simplified representation of the schematic circuit diagram for this case is shown in FIG. 10B. The NAFION material membrane is inert and will not be affected by the corrosive liquid, nor will it affect the corrosion mechanism.

The embodiments described above are illustrative of the inventive design and construction of probes utilizing the NAFION material elements for measuring corrosion rates of liquid media having high or low ionic conductivity. One unique feature of the invention is utilization of the probe 50 to measure the corrosion rate in low conductivity media. Other designs and variations may become apparent to a person of ordinary skill in the art once an appreciation of the invention is attained. Accordingly, the scope of the invention is not limited by the disclosed embodiments.

We claim:

1. An apparatus for measuring metal corrosion rate in a solution comprising:
   a) a counter electrode for providing current;
   b) a reference electrode to sense the potential of a working electrode;
   c) a working metal electrode being of the material of which the corrosion rate is being determined; and
   d) an ionic conducting material disposed at least between the reference and working metal electrodes for providing a pathway for ionic conduction between the working and reference electrodes, wherein the ionic conducting material comprises a polymeric perfluorinated material including polypropylene oxide side chain branches terminating in a group chosen from sulfonic acid and carboxylic acid.

2. The apparatus according to claim 1 wherein the ionic conducting material further comprises a solid material having the composition 3. The apparatus according to claim 2 wherein said ionic conducting material is in the form of a washer which is removable from contact between the electrodes.

4. The apparatus according to claim 1 wherein the ionic conducting material further comprises a solid material having the composition 5. The apparatus according to claim 4 wherein said ionic conducting material is in the form of a washer which is removable from contact between the electrodes.

6. The apparatus according to claim 1 wherein said reference electrode comprises a reference cell.

7. The apparatus according to claim 6 wherein said reference cell further comprises an Ag/AgCl reference cell.

8. The apparatus according to claim 1 wherein said ionic conducting material is disposed between the reference electrode, the working metal electrode, and the counter electrode.

9. The apparatus according to claim 1 wherein said ionic conducting material is in the form of a washer which is removable from contact between the electrodes.

10. A method of measuring corrosion rate of a predetermined metal in a solution comprising:
   a) providing a probe, including a counter electrode, a reference electrode, and a working metal electrode in close proximity to each other and electrically insulated one from another, said working metal electrode comprising the predetermined metal of which corrosion rate is being measured;

b) disposing an electrically insulating but ion conducting material between at least the reference electrode and the working metal electrode for transmitting ions between them, said ionic conducting material comprising a polymeric perfluorinated material including polypropylene oxide side chain branches terminating in a group chosen from sulfonic acid and carboxylic acid;

c) contacting the probe to the test solution;

d) measuring the potential between the reference and working metal electrodes;

e) analyzing the potential to determine a value of the polarization resistance between the working metal electrode and the reference electrode; and f) calculating the corrosion rate from the value of polarization resistance obtained in step e.

11. The method according to claim 10 wherein said ionic conducting material is in the form of a washer which is removable from contact between the electrodes.

* * * * *